(12) United States Patent
Sainath et al.

(10) Patent No.: US 8,483,361 B2
(45) Date of Patent: Jul. 9, 2013

(54) ANODE TARGET FOR AN X-RAY TUBE AND METHOD FOR CONTROLLING THE X-RAY TUBE

(75) Inventors: Paavana Sainath, Oconomowoc, WI (US); Xiaoye Wu, Rexford, NY (US); Girijesh K. Yadava, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 289 days.

(21) Appl. No.: 12/976,950

(22) Filed: Dec. 22, 2010

(65) Prior Publication Data
US 2012/0163530 A1    Jun. 28, 2012

(51) Int. Cl.
*H01J 35/30* (2006.01)
(52) U.S. Cl.
USPC .............. 378/137; 378/125; 378/144
(58) Field of Classification Search
USPC .............. 378/121, 125, 137, 143, 144, 156
See application file for complete search history.

(56) References Cited

U.S. PATENT DOCUMENTS

| | | | |
|---|---|---|---|
| 2005/0084060 A1* | 4/2005 | Seppi et al. | 378/5 |
| 2008/0080662 A1* | 4/2008 | Shukla | 378/4 |
| 2010/0080357 A1* | 4/2010 | Katcha et al. | 378/124 |

* cited by examiner

*Primary Examiner* — Courtney Thomas
(74) *Attorney, Agent, or Firm* — The Small Patent Law Group; Dean D. Small

(57) ABSTRACT

Anode targets for an x-ray tube and methods for controlling x-ray tubes for x-ray systems are provided. One x-ray system includes a field-generator configured to generate a field, an electron beam generator configured to generate an electron beam directed towards a target and a voltage controller configured to control the electron beam generator to produce an electron beam at a first energy level and an electron beam at a second energy level. The x-ray system also includes a field-generator controller configured to control a field to deflect at least one of the electron beams, wherein the electron beam, at the first energy level, impinges on the target at a first contact position and the electron beam, at the second energy level, impinges on the target at a second contact position. The at the first contact position and at the second contact position is configured to filter x-rays.

20 Claims, 10 Drawing Sheets

ANODE TARGET FOR AN X-RAY TUBE AND METHOD FOR CONTROLLING THE X-RAY TUBE

BACKGROUND OF THE INVENTION

The subject matter disclosed herein relates generally to x-ray tubes used in imaging systems and more particularly, to x-ray tubes generating two different energy levels of x-rays.

Typically, in computed tomography (CT) imaging systems, an x-ray source emits a fan-shaped beam toward a subject or object, such as a patient or a piece of luggage. The beam, after being attenuated by the subject, impinges upon an array of radiation detectors. The intensity of the attenuated beam radiation received at the detector array is typically dependent upon the attenuation of the x-ray beam by the object. Each detector element of the detector array produces a separate electrical signal indicative of the attenuated beam received by each detector element. The electrical signals are transmitted to a data processing system for analysis which ultimately produces an image.

Material decomposition involves measuring an x-ray absorption characteristic of a material for two different energy levels of x-rays. Dual energy scanning can be used to obtain diagnostic CT images that enhance contrast separation within the image by utilizing two scans at different chromatic energy states. A number of techniques are known to achieve dual energy scanning, including acquiring two back-to-back scans sequentially in time where the scans require two rotations around the object in which the tube operates at, for instance, 80 kVp and 140 kVp potentials. Alternatively, two-tube-two-detector architecture enables acquiring two scans simultaneously, but with a difference in phase. Taking separate scans several seconds apart from one another or acquisitions that are different in phase result in mis-registrations between datasets caused by patient motion (both external patient motion and internal organ motion). Additionally, a dual-tube, dual-detector system also results in poor registration of data acquired at two energies and introduces artifacts due to the difference in acquisition time and phases respectively.

BRIEF DESCRIPTION OF THE INVENTION

In accordance with an embodiment, an x-ray system is provided that includes a field-generator configured to generate a field, an electron beam generator configured to generate an electron beam directed towards a target and a voltage controller configured to control the electron beam generator to produce an electron beam at a first energy level and an electron beam at a second energy level. The x-ray system also includes a field-generator controller configured to control a field to deflect at least one of the electron beams, wherein the electron beam, at the first energy level, impinges on the target at a first contact position and the electron beam, at the second energy level, impinges on the target at a second contact position. The target, at the first contact position and at the second contact position, is configured to filter x-rays.

In accordance with another embodiment, a method of filtering dual energy x-ray is provided. The method includes generating electron beams, directing the generated electrons beam towards a target and controlling the voltage of the electron beams to produce an electron beam at a first energy level and an electron beam at a second energy level. The method also includes generating a field and controlling the generated field to deflect at least one of the electron beams, wherein the electron beam, at the first energy level, impinges on the target at a first contact position and the electron beam, at the second energy level, impinges on the target at a second contact position. The method further includes filtering the x-ray produced at the first contact position using the target and filtering the x-ray produced at the second contact position using the target.

In accordance with yet another embodiment, a target for an x-ray tube is provided that includes a first contact area and a second contact area different than the first contact area. The first and second contact areas are formed from different materials or provided at different angles, and configured to receive thereon differently deflected electron beams.

DETAILED DESCRIPTION OF THE INVENTION

Figure 1:
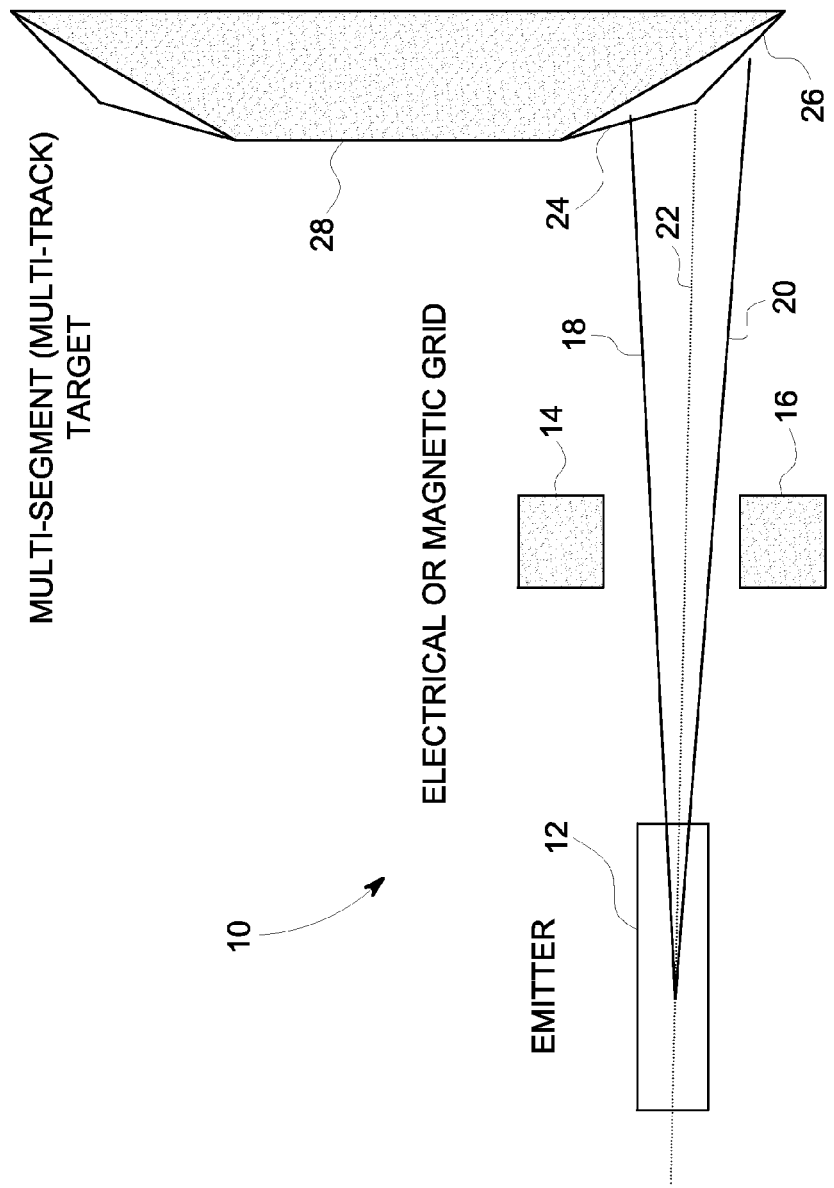
FIG. 1 illustrates a multi-segment or multi-track target formed in accordance with an embodiment and illustrating different electron beams.

The foregoing summary, as well as the following detailed description of certain embodiments of the subject matter disclosed herein, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like, or multiple pieces of hardware) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings, nor are the figures necessarily drawn to scale.

As used herein, an element or step recited in the singular and proceeded with the word "a" or "an" should be understood as not excluding plural said elements or steps, unless such exclusion is explicitly stated. Furthermore, references to "one embodiment" of the subject matter disclosed herein are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Also, in the subject matter disclosed herein the words "target" and "anode" may be used interchangeably. Additionally, the recitation of a particular number of elements does not exclude embodiments having more than that particular number, unless the number is further qualified by words such as "exactly" or "only." Also, unless the possibility is either explicitly, logically, or physically excluded, individual features may be omitted from an embodiment, or one or more features from another embodiment or other embodiments, may be combined to produce additional embodiments of the subject matter disclosed herein.

Hereinafter, the terms "subject" and "object" shall include anything capable of being imaged. Also, as used herein, the phrase "reconstructing an image" is not intended to exclude embodiments of the subject matter disclosed herein in which data representing an image is generated, but a viewable image is not. Therefore, as used herein the term "image" broadly refers to both viewable images and data representing a viewable image. However, many embodiments generate (or are configured to generate) at least one viewable image. Additionally, although described in detail in a computed tomography (CT) medical setting, it is contemplated that the benefits accrue to all imaging modalities including, for example, ultrasound, Magnetic Resonance Imaging, (MRI), Electron Beam CT (EBCT), Positron Emission Tomography (PET), Single Photon Emission Computed Tomography (SPECT), and in both medical settings and non-medical settings such as an industrial setting or a transportation setting, such as, for example, but not limited to, a baggage scanning CT system for an airport or other transportation center.

Various embodiments may be implemented in connection with different types of imaging systems. For example, various embodiments may be implemented in connection with a CT imaging system in which an x-ray source using focal spot deflection (multiple focal spots may be provided) projects a fan-shaped beam that is collimated to lie within an X-Y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. In an axial scan (e.g., a step-and-shoot axial scan), the projection data is processed to construct an image that corresponds to a two-dimensional slice taken through the object. One method for reconstructing an image from a set of projection data is referred to in the art as a filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, a patient or object (e.g., baggage) is moved while the data for a prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighting algorithms that weight the acquired data as a function of view angle and detector channel index. Specifically, prior to a filtered back-projection process, the data is weighted according to a helical weighing factor, which is a function of both the gantry angle and the detector angle. The weighted data is then processed to generate CT numbers and to construct an image that corresponds to a two-dimensional slice taken through the object.

FIG. 1 illustrates a multi-segment or a multi-track target system 10 with different electron beams formed in accordance with an embodiment. The illustrated embodiment may be used with an x-ray source and rapid kilovolt peak (kVp) switching along with synchronized switching of the field to focus the electron beam at different focal spots. The x-ray generator can produce rapid kVp switching for an x-ray tube, with an electrical or magnetic grid providing deflection of the electron beams.

In various embodiments an electron beam is produced at an emitter 12 and is deflected using the fields produced at 104, 106, for example, by an electrical or magnetic grid. In one embodiment, an electron beam 18 with a lower kVp is deflected to interact with the target (anode) 28 at an area 26, which may define a focal spot or first contact position. For example, an 80 kVp electron beam may be deflected to hit the anode 28 at the area 26. Additionally, an electron beam 20 with a higher kVp is deflected to interact with the target (anode) 28 at an area 24, which may define a focal spot or second contact position. For example, a 140 kVp electron beam may be deflected to hit the anode 28 at the area 24. It should be noted that the electrons beams 18 and 20 may be provided at any kVp level and that are deflected from an axis 22.

The system 10 may be used, for example, for performing material decomposition in a dual-monoenergetic x-ray system. In various embodiments, material decomposition is provided by separating two x-ray energy spectra such that there would have less overlap between the low-energy x-ray and the high-energy x-ray. Accordingly, the system 10 may provide dual-energy operation using suitable target angles and/or suitable target material or a combination of target angle and target material.

The dual or segmented track anode can be provided in one of several different configurations enabling differential filtration or tube exit spectra between the high and low energies. The lower energy x-rays in a fast-switching dual energy acquisition are focused on the portion of the target or focal track that would preserve the lower energy x-rays with reduced or minimum self-filtration. This can be achieved by using a focal track with a larger angle or by reducing the amount of high z material filtration by changing the thickness of the filtering material on the focal track, where "high z" material may be a material with a higher atomic weight.

The higher energy x-rays in fast-switching dual energy acquisitions are deflected or focused on the portion of the target or focal track that would enable higher or maximum filtration of the lower energies (that overlap with the low energy spectrum). This can be achieved by using a focal track with a smaller angle or by increasing the amount of the high z material filtration by changing the thickness of the filtering material on the focal track.

Depending on the angle of the impinging electron beam there is an inherent filtration of the generated x-rays. An electron beam's penetration into a target depends in part on the angle of the impinging electron beam. Therefore, at different impinging angles the electron beam penetrates to different depths of the target. As these impinging electron beams generate the x-rays, x-rays exit the target from different depths. For example, the target surface at a first angle will allow different penetration of the electron beam compared to the target surface with a second angle, wherein the first angle of the target surface is different than the second angle of the target surface. The target material filters these x-rays as the x-rays exit the target material. Such inherent filtration of the x-ray is evident in cone beam CT, where the x-ray cone has different energy x-rays at different positions.

Accordingly, the anode 28 may have focal spots at the areas 24 and 26 that comprise different target materials for filtration of generated x-rays. For example, the target focal spot may be formed of a material of lower atomic weight for low energy x-rays. Alternatively, the target focal spot may be made of material of higher atomic weight for high energy x-rays. In an alternate embodiment the focal spot for a lower energy beam and a higher energy beam may have be formed of a same base material, but may be coated with a material with a different atomic weight. For example, the filtering material, for a focal spot, may be tungsten. In another alternate embodiment, the focal spot may be made of a same material, but may have different thickness for the lower energy and the higher energy areas. For example, the thickness of the lower energy focal spot may be less than the thickness of the higher energy. In another alternate embodiment, the target may be a combination of any of the above embodiments.

In various embodiments, it is desirable to maintain the focal spot size change while changing the focal track. The focal spot optical size in the z-axis is defined by both the width of the electron beam in the y-axis as well as the angle of the focal track. The grid used to focus the electron beam is configured to match the size of the focal spot in z between the low and higher energy views. The grid that controls the focal spot y-axis dimension is rapidly switched to enable an alternative increase and decrease y-axis dimension of the electron beam to compensate for the focal track angle change, such that the optical focal spot size remains constant. It should be noted that other suitable methods to control the focal spot size may be used.

In various embodiments, the low and high kVp data is reconstructed to compensate for the change in source to detector distance with the switching of the electron beam between two tracks. Different methods may be used to align the data between the high and low kVp views. One method includes interpolation techniques to align the high and low kVp samples. Another method separates the high and low kVp views into two separate sinograms and performs an independent reconstruction of each. These reconstructions are then synthesized back into projections such that the data from low and high kVp are aligned. Further, the material decomposition processing is performed on these synthesized projections or the back-projected images in the image space. It should be noted that other suitable methods to compensate for the change in source distance may be used.

Figure 2:
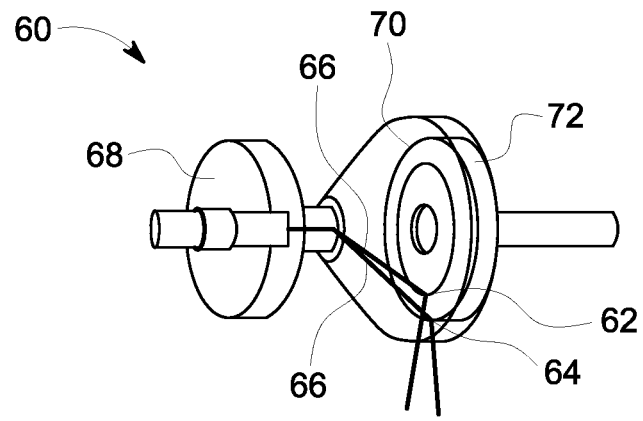
FIG. 2 is a pictorial representation of an x-ray tube that uses focal spot deflection for performing x-ray imaging in accordance with an embodiment.

FIG. 2 is a pictorial representation of an x-ray tube 60 that uses focal spot deflection for performing x-ray imaging, in accordance with an embodiment. It should be noted that the various embodiments may be implemented in connection with any type of x-ray tube 60 that can deflect focal spots in the z-direction and are not limited to the x-ray tube 60 illustrated in FIG. 2. Moreover, the focal spot deflection may be provided using any known method, for example, using an electromagnetic field or an electrostatic field generated by an electromagnetic field source or an electrostatic field source, respectively. Other methods of producing multiple focal spots also may be used. For example, multiple focal spots in the z-direction may be produced using nano-tube technology, multiple anodes and cathodes in an x-ray tube 60, or by placing multiple small x-ray tubes along the z-axis.

The x-ray tube 60 utilizes multiple focal spots 62 and 64 (two focal spots are illustrated) spaced along the target radial direction. A cathode 68 of the x-ray tube 60 generates electron beams 66 that are deflected dynamically in some embodiments using a magnetic field such that the focal spots 62 and 64 are spaced apart on a target 70 of an anode 72 (e.g., a rotating anode), which may be embodied as the anode 28 (illustrated in FIG. 1). The target 70 may be an annular shaped element on the anode 72. Cooling of the components of the x-ray tube 60 may also be provided using any known manner (e.g., liquid cooling system).

Figure 3:
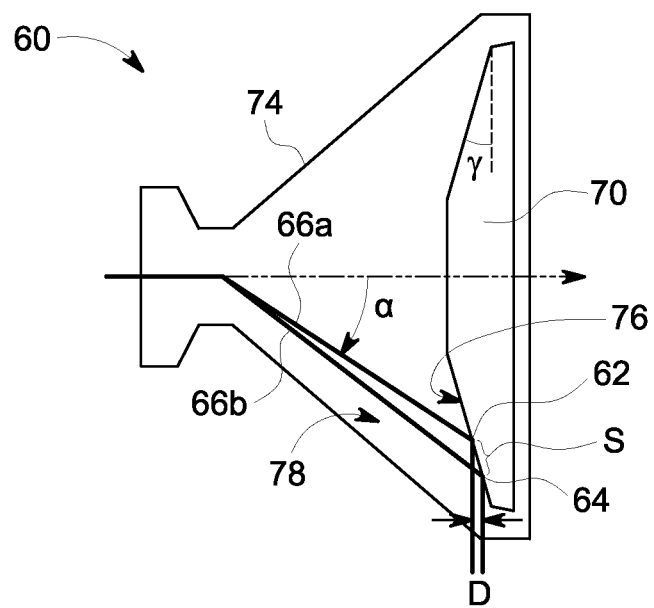
FIG. 3 illustrates a focal spot deflection in an x-ray tube in accordance with an embodiment.

In operation, when the magnetic field changes quickly, the electron beams 66 can be directed at two different locations on the target 70 to produce two distinct focal spots 62 and 64 that may be separated by small distance S in the z-direction as shown in FIG. 3, for example, six millimeters (mm). The components of the x-ray tube 60 in FIG. 3 are shown in a housing 74.

In various embodiments, and for example, in order to minimize aliasing artifacts in the z-direction, the spacing between the two focal spots 62 and 64 on the target 70 is provided such that the x-rays connecting one of the focal spots 62 or 64 to the detector cells interlace the x-rays connecting the other focal spot 64 or 62 to the detector cells in the z-direction. For illustrative purposes only, and based on a detector-to-iso distance of 408 mm and a projected cell spacing at the iso-center of 0.625 mm, the deflection distance D in the z-direction may be 0.73 mm. In another example, for a target 70 having an angled portion 76 (e.g., an angled outer surface) with an angle of 7 degrees (i.e., the angle between the target surface and the x-y plane), the distance between the two focal spots 62 and 64 along the target surface 78 is determined as follows: 0.73/sin (7°)=5.96 mm. Accordingly, by changing the amount of the deflection angle (a) and/or the target angle (g), the spacing of the focal spots 62 and 64 on the target 70 can be increased even more (e.g., significantly or substantially increased). For example, with a spacing of 50 mm along the target surface 78 as shown in FIG. 3, a difference in the deflection angles between the electron beams 66a and 66b results in an increased target angle (g).

Accordingly, use of focal spot deflection and the angled portion 76 provides increased spacing between the two focal spots 62 and 64. For example, if the two focal spots 62 and 64 are separated in the z-direction (referred to as the twin peak concept), cone beam artifacts for a large coverage area are reduced. For illustrative purposes only, for a detector z-coverage of 100 mm at the iso-center, an 80 mm spacing between the two focal spots 62 and 64 can produce images nearly free of cone beam artifacts in the step-and-shoot mode acquisition. It should be noted that that the spacing of the focal spots 62 and 64 along the target surface 78 is magnified by the factor 1/sin(g) as compared to the spacing of the focal spots 62 and 64 in the z-direction. It also should be noted that when g is less than 45 degrees, the spacing along the target surface 78 is always larger than the spacing along the z-direction.

Figure 5:
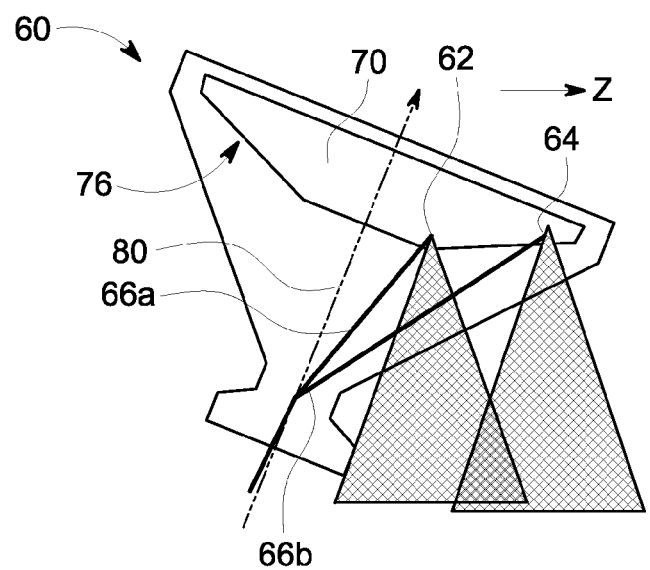
FIG. 5 illustrates the target of a focal spot deflected x-ray tube aligned with a z-axis in accordance with an embodiment.

In various embodiments, and to provide increased spacing between the focal spots, the target surface 78, for example, the angled portion 76 is aligned with the z-axis as shown in FIG. 3. For example, the x-ray tube 60 is offset from the z-axis. For example, the cathode 68 (shown in FIG. 2) that extends along a longitudinal axis of the x-ray tube 60 is offset from the z-axis. In some embodiments, the x-ray tube 60 may be mounted in an offset orientation on the gantry 1212 (shown in FIG. 12). For example, the radiation source 1214 (shown in FIG. 12) may be provided in an offset orientation on the gantry 1212 such that a target of the radiation source 1214 is aligned with the gantry rotation axis or z-axis. It should be noted that the x-ray tube 60 may be mounted in a fixed orientation or may be movable (e.g., pivotally mounted), which movement may be provided manually by hand or mechanically using a motor, which may be provided dynamically. For example, the x-ray tube 60 may be rotated in an axis parallel to the z-axis and about a pivot point 80 as shown in FIG. 5.

Modifications and variations to the various embodiments may be provided. For example, the x-ray tube 60 axis may be tilted with respect to the z-axis so that the amount of tilt is adjusted such that the spacing between a plurality of focal spots can be changed. As another example, the gantry 1212 may remain stationary during data acquisition with the plurality of focal spot along the z-axis producing increased coverage for an x-ray radiographic mode of imaging. The mode serves, for example, as a pre-screening for a CT procedure.

Figure 12:
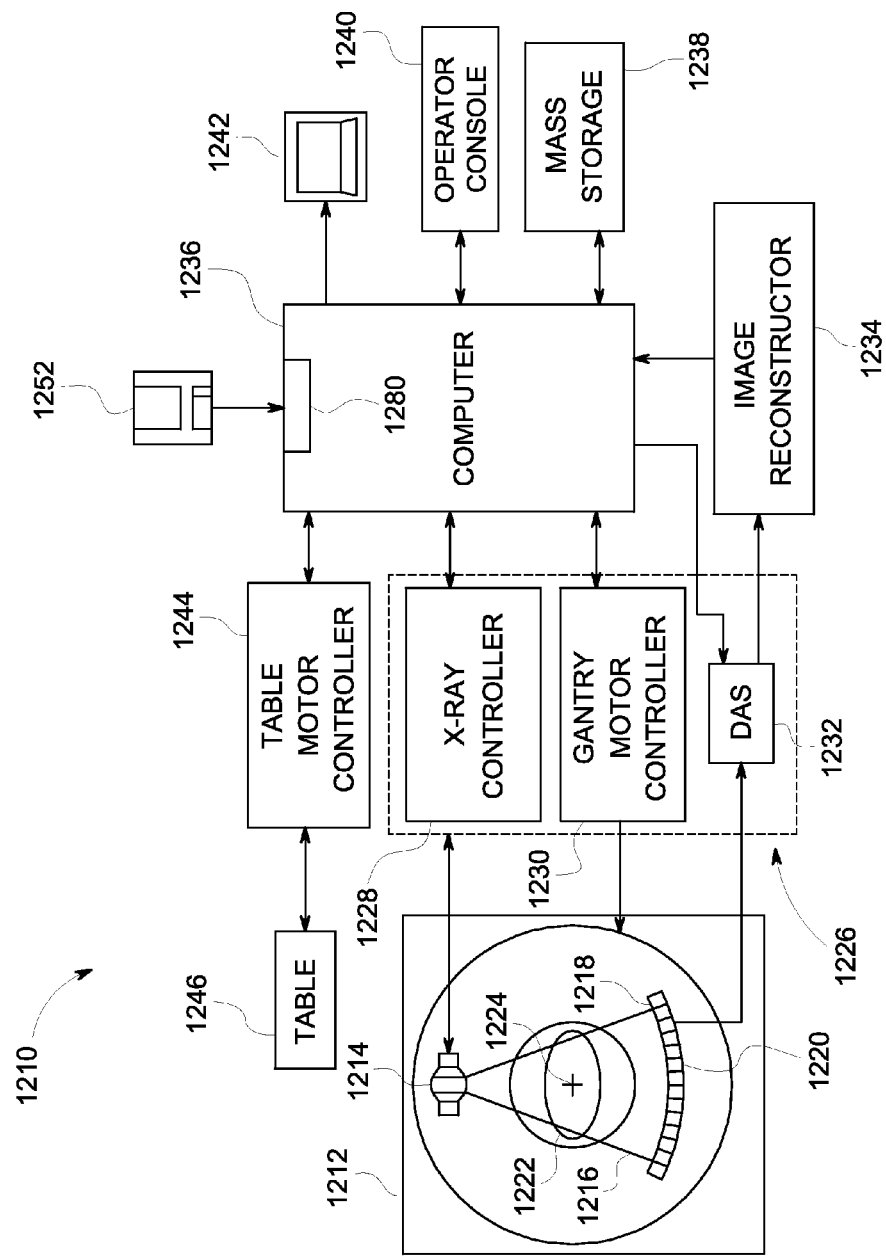
FIG. 12 is a block diagram of a CT imaging system constructed in accordance with an embodiment.

As a further example, the x-ray tube 60 may be used in the x-ray radiography mode of the CT imaging system 1210 (shown in FIG. 12). In this mode, the gantry 1212 does not rotate with respect to the patient 1222. The two focal spots 62 and 64 are turned on sequentially to enable a large coverage of the patient 1222 in the z-direction so that an x-ray radiographic image of, for example, the entire organ is obtained. In order to enhance the spatial resolution, the x-ray focal spot can be deflected slighted in the x-direction and z-direction to achieve double sampling. As still a further example, the x-ray tube 60 can be used for tomosynthesis data acquisition in which the gantry 1212 remains stationary while the motorized table 1246 translates.

Thus, in various embodiments, a tilted tube CT system may be provided and that operates as an x-ray radiography or tomosynthesis device to provide semi-tomographic capability. As a result of the significantly reduced radiation dose compared to a normal CT scan operation, the radiography mode or the tomosynthesis mode can be used, for example, for pre-screening to determine the need for a normal or complete CT scan.

Figure 6:
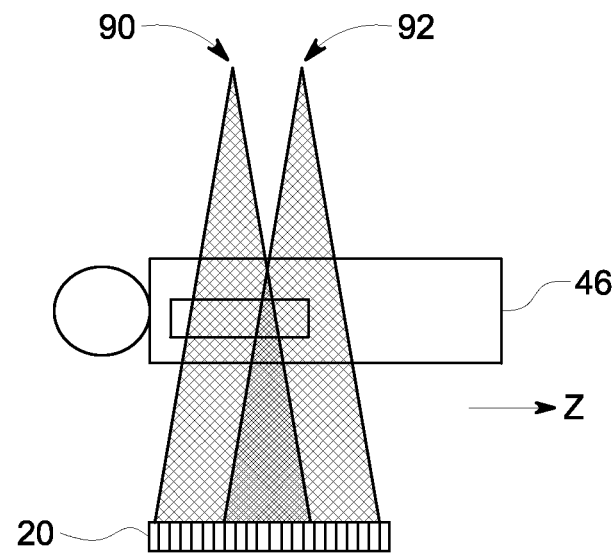
FIG. 6 illustrates a radiography mode of operation performed in accordance with an embodiment.
Figure 7:
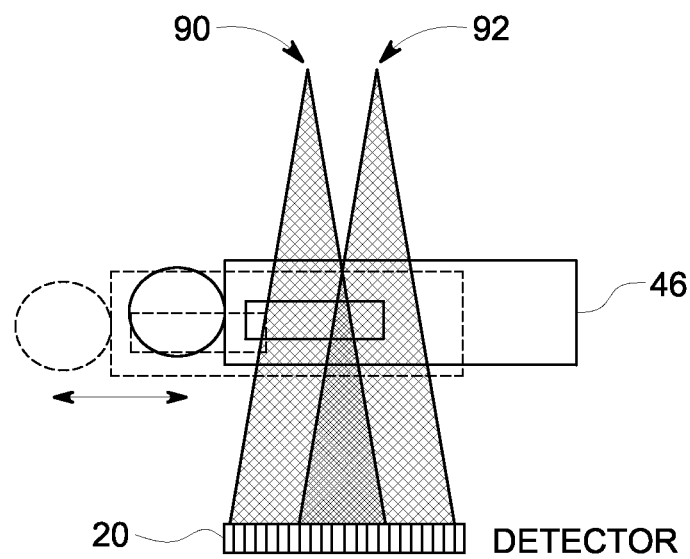
FIG. 7 illustrates a tomosynthesis mode of operation performed in accordance with an embodiment.

In particular, in the radiography mode as illustrated in FIG. 6, both the gantry 1212 (shown in FIG. 12) and a motorized table 1246 remain stationary. Sequential deflected focal spots 90 and 92 provide increased z-direction coverage. It should be noted that additional focal spot deflection in the x-direction and z-direction can also be used to produce interlaced samples in x and z to enhance spatial resolution. In the tomosynthesis mode as illustrated in FIG. 7, the gantry 1212 (shown in FIG. 12) remains stationary, but the motorized table 1246 translates along the z-axis. The two focal spots 90 and 92 are turned on sequentially (with deflection) during table translation. Because each point in the scanned object is viewed from several different angles as the motorized table 1246 moves (represented by the arrow), a tomosynthesis effect can be produced. Further, using various algorithms known in the art, images can be generated that partially remove the overlapping structures and enable better visualization of the object.

Figure 8:
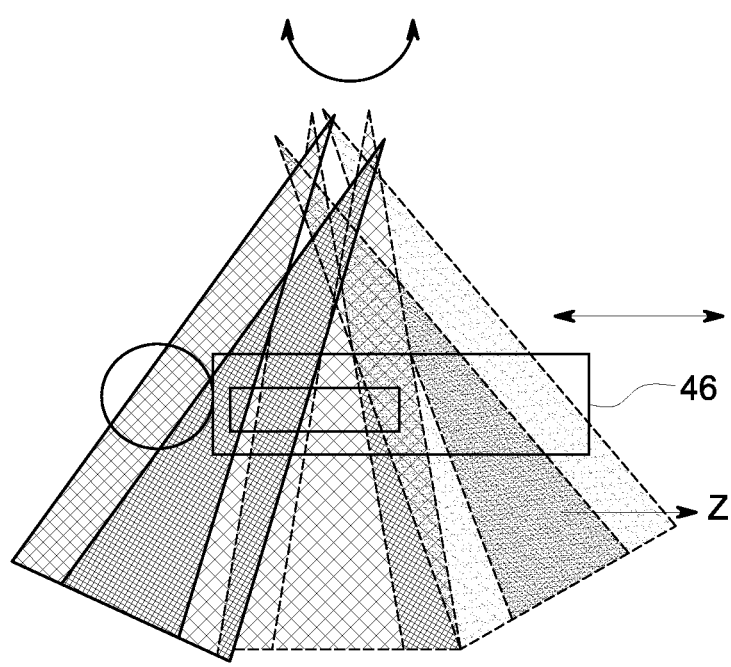
FIG. 8 illustrates a pivoting x-ray tube during a tomosynthesis mode of operation in accordance with an embodiment.

To further enhance the tomosynthesis effect, the x-ray tube 60 can be pivoted as illustrated in FIG. 8 to provide additional angular range during data acquisition. During a scan, the x-ray tube 60 axis is dynamically adjusted while the motorized table 1246 translates (represented by the arrow).

Figure 9:
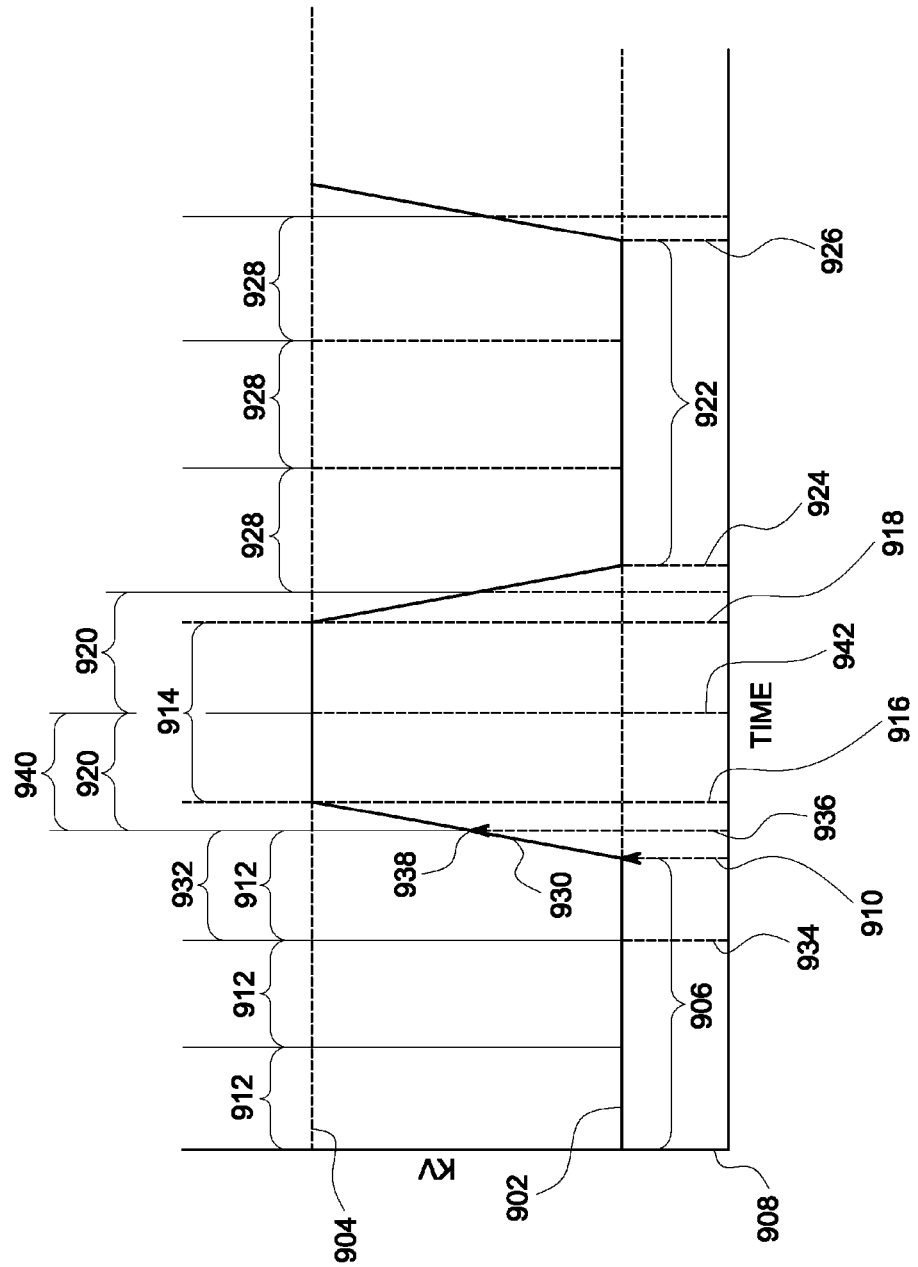
FIG. 9 is a timing diagram of a low and high kVp protocol in accordance with an embodiment.

FIG. 9 is a plot illustrating a timing diagram of a low and high kVp protocol that may be performed in various embodiments. As used herein, imaging data, in this and related embodiments, may also be referred to as views or as projections. The imaging data is acquired at a first voltage 902 according to an embodiment of the subject matter disclosed herein. Additionally, the imaging data is acquired at a second voltage 904. In this embodiment, the x-ray generator controlled by a controller provides the first voltage 902 to the x-ray tube 60 for a first duration 906. For example, the first duration 906 starts at a time 908 and ends at a time 910. During the first duration 906, one or more views 912 may be acquired at the first voltage 902. After the first duration 906, the x-ray generator provides the second voltage 904 to the x-ray tube 60 for a second duration 914, starting at time 916 and providing the second voltage 904 until a time 918. During the second duration 914, two or more views 920 may be acquired at the second voltage 904. After the second duration 914, the x-ray generator may again be caused to supply the first voltage 902 to the x-ray tube 60 for a third duration 922, starting at time 924 and providing the first voltage 902 until a time 926. During the third duration 922, one or more views 928 of data may be acquired at the first voltage 902. For example, the first voltage 902 is 80 kVp and the second voltage 904 is 140 kVp. The electrical current of the x-ray tube 60 is controlled as a function of the applied voltages 902, 904. In one embodiment, the total number of views acquired in 906 and 914 may be the same. Alternatively, the number of views acquired within time duration 906 may be different than the number of views acquired within time duration 914.

Because of capacitive and other effects, the x-ray generator is not capable of instantaneously switching from the first voltage 902 to the second voltage 904 and vice versa. As such, a finite time is typically required to allow for a voltage change to be achieved. For example, the x-ray generator may be at the first voltage 902 until time 910. At time 910, when the x-ray generator is caused to output the second voltage 904, and the output of the generator will not achieve the second voltage 904 until a later time 916. Thus, a transition time 930 occurs from time 910 to time 916 during which the x-ray generator voltage transition between the two voltages 902, 904.

In order to avoid delaying an acquisition of view data at the second voltage 904 after acquiring view data at the first voltage 902 such that view data is acquired only when the second voltage 904 is actually achieved, view data may be acquired during the transition 930. In this manner, view data at the first voltage 902 may be acquired in one portion of transition 930, and view data at second voltage 904 may be acquired in another portion of transition 930. As shown, views 912 at the first voltage 902 include a last view 932, which is started at a time 934 and ends at a time 936 substantially corresponding to a point 938 of the transition 930. Accordingly, the view 932, in addition to including view data acquired at first voltage 902, includes view data acquired at voltages above the first voltage 902 and below a voltage of the point 938 between voltages 902, 904. Once the voltage of the x-ray tube 60 passes point 938, the view 932 is complete, and acquisition of view data in a first view 940 of views 920 begins. As such, the first view 940 is started at time 936 and ends at time 942, which includes a voltage at second voltage 904.

A computer 1236 (shown in FIG. 12) may be configured to reduce or minimize x-ray dose received by the patient 1322, by controlling the timing of signals to the x-ray generator. The view 932 acquired at the first voltage 902 may include data collected while the output voltage of the generator is in transition between the time 910 and 936. Furthermore, the first view 940 of data including data acquired at the second voltage 904 may be triggered at the time 936 to occur prior to the output voltage achieving the second voltage 904. In one embodiment, the trigger point 938 occurs substantially halfway between the first voltage 902 and the second voltage 904. Alternatively, the trigger may not be at a point halfway between the two voltages 902, 904, but may be at some different point between the two voltages. For example, the pattern of low and high voltages may be repeated for different times and, accordingly, at different gantry angles such that an interleaved pattern of data is acquired with one or more views obtained at the first voltage 902, two or more views obtained at the second voltage 904, and one or more views obtained again at the first voltage 902. The number of views captured need not be limited to the pattern as illustrated (i.e., three views at the first voltage 902, two views at the second voltage 904, and three views again at the first voltage 902). For example, the views captured may range from 2-50 views for a few tens of milliseconds (msec) at each kVp before switching back to the other kVp. Alternatively, the switching of kVp may be done so as to obtain one view per voltage level.

Figure 10:
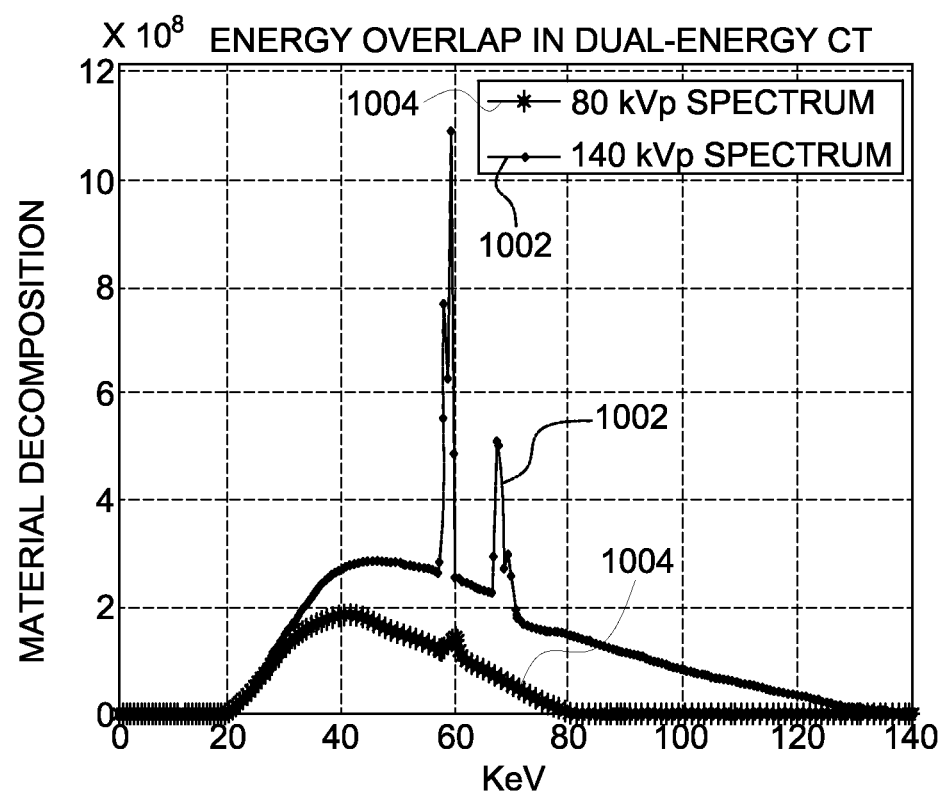
FIG. 10 illustrates energy overlap in dual energy computed tomography (CT) without filtration.

FIG. 10 illustrates energy overlap in dual energy CT without filtration. As shown in the graph, a curve 1002 represents the high energy x-ray spectrum. Also, as shown in the graph, a curve 1004 represents the low energy x-ray spectrum. For example, the low energy spectrum may be 80 kVp and the high energy spectrum may be of 140 kVp. Alternatively, the low energy spectrum may range from 60 kVp to 100 kVp. Alternatively, the high energy spectrum may range from energy levels of 120 kVp and above. As shown in FIG. 10, there is significant overlap between low energy spectrum and high energy spectrum at the low energy range.

Figure 11:
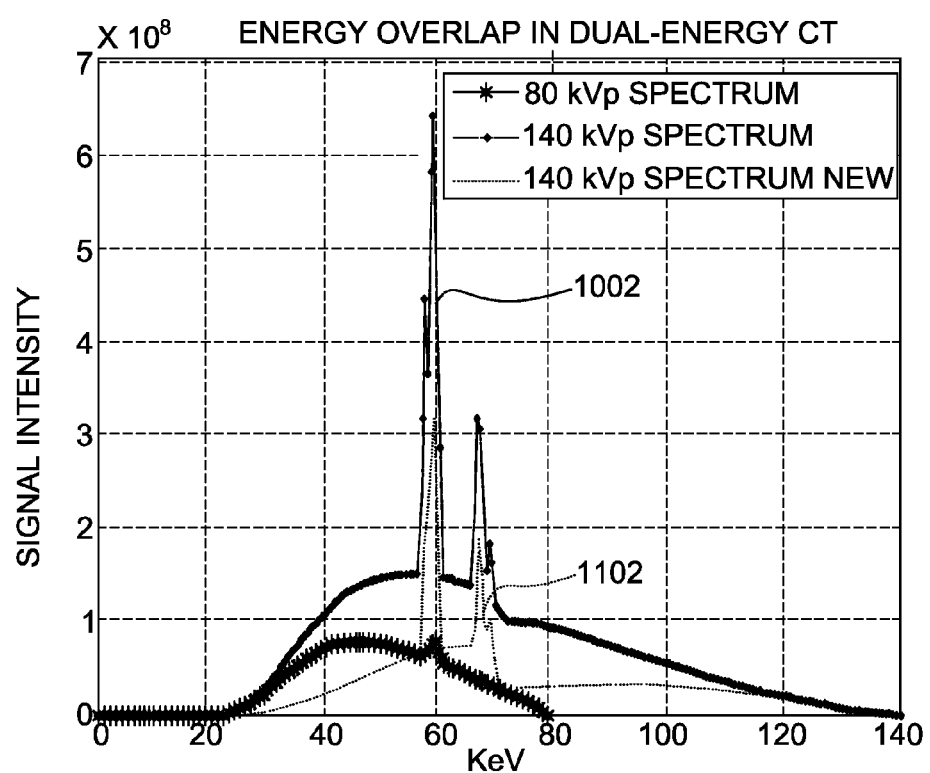
FIG. 11 illustrates energy overlap reduction in dual energy CT in accordance with an embodiment.

FIG. 11 illustrates energy overlap reduction in dual energy CT, in accordance with an embodiment. FIG. 11 is one example of the reduction in spectral overlap using an x-ray tube 60 configured with different focal spot angles for low energy and high energy spectrum. The higher energy spectrum (in this case, 140 kVp spectrum) has reduced overlap with the lower energy spectrum increasing the mean keV separation compared to the spectrum in FIG. 10. For example, curve 1102 represents the curve 1002 after filtration. The curve 1102 demonstrates reduced energy overlap between curve 1102 and curve 1004. As evident from FIG. 11, the curve 1102 has no energy x-rays below 30 kVp. Also, evident from FIG. 11, the filtering of low energy spectrum from the high-energy x-ray beam creates the higher energy and low energy spectrum with no overlap between 30 kVp to 80 kVp. Hence, the two energy spectrums are well discriminated between lower energies and higher energies. Furthermore, the filtration process reduces noise and further enhances separation of the lower and higher energy x-ray spectrum.

In a dual energy scan, two x-ray spectrums are produced simultaneously at different kVp levels. The result is two CT data sets, allowing differentiating, characterizing, isolating, and distinguishing the imaged material. Once such application of dual energy CT may be the differentiating, characterizing, isolating, and distinguishing of cysts from cancerous lesions in liver. Enhancement patterns of liver lesions can clearly be visualized with the dual energy CT, particularly using the various embodiments disclosed herein. Another example of a use for various embodiments disclosed here is measuring of bone mineral density (BMD). BMD can be determined from the absorption of each energy spectrum by bone. Yet another example of a use for various embodiments disclosed here is differentiating, characterizing, isolating, and distinguishing of pulmonary nodules.

Additionally, dual energy CT with improved differentiation between lower energy and higher energy spectrum can help reduce beam-hardening artifacts. Such artifacts are generally encountered in cranial scanning. Having two energy spectrums eliminates the beam hardening. Further, inherent filtration of x-ray spectrum helps improve fidelity of signal to background noise. Moreover, the contrast to noise ratio as measured by the difference between the CT numbers of two objects is enhanced by having a clear difference between the lower energy and higher energy x-ray spectrum.

FIG. 12 shows at CT imaging system 1210 having a radiation source 1214 (having an x-ray tube formed in accordance with various embodiments as described herein) and a multislice detector array 1218 having only a single row of detector elements 1220 (i.e., a detector row). However, the multislice detector array 1218 includes a plurality of parallel detector rows of detector elements 1220 such that projection data corresponding to a plurality of quasi-parallel or parallel slices can be acquired simultaneously during a scan.

Rotation of the gantry 1212 and the operation of the radiation source 1214 (and optionally movement of the radiation source 1214) are governed by a control mechanism 1226 of the CT imaging system 1210. The control mechanism 1226 includes a radiation controller 1228 that provides power and timing signals to the radiation source 1214 and a gantry motor controller 1230 that controls the rotational speed and position of the gantry 1212. A data acquisition system (DAS) 1232 in the control mechanism 1226 samples analog data from the detector elements 1220 and converts the data to digital signals for subsequent processing. An image reconstructor 1234 receives sampled and digitized radiation data from the DAS 1232 and performs high-speed image reconstruction. The reconstructed image is applied as an input to a computer 1236 that stores the image in a mass storage device 1238.

The computer 1236 also receives commands and scanning parameters from an operator via a console 1240 that has, for example, a keyboard and/or other user input device(s). An associated display system 1242 allows the operator to observe the reconstructed image and other data from the computer 1236. The operator supplied commands and parameters are used by the computer 1236 to provide control signals and information to the DAS 1232, the radiation controller 1228 and the gantry motor controller 1230. In addition, the computer 1236 operates a table motor controller 1244 that controls a motorized table 1246 to position the patient 1222 in the gantry 1212 or to move the patient 1222 along the z-axis. In particular, the table 1246 moves portions of the patient 1222 through the gantry opening 1348.

In one embodiment, the computer 1236 includes a device 1250, for example, a floppy disk drive, CD-ROM drive, or DVD-ROM drive, for reading instructions and/or data from a computer-readable medium 1252, such as a floppy disk, CD-ROM, or DVD. It should be understood that other types of suitable computer-readable memory are recognized to exist (e.g., CD-RW and flash memory, to name just two), and that this description is not intended to exclude any of these. In another embodiment, the computer 1236 executes instructions stored in firmware (not shown). Generally, a processor in at least one of the DAS 1232, the reconstructor 1234, and the computer 1236 shown in FIG. 12 is programmed to execute the processes described below. However, the method is not limited to practice in the CT imaging system 1210 and can be utilized in connection with many other types and variations of imaging systems. In one embodiment, the computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 13:
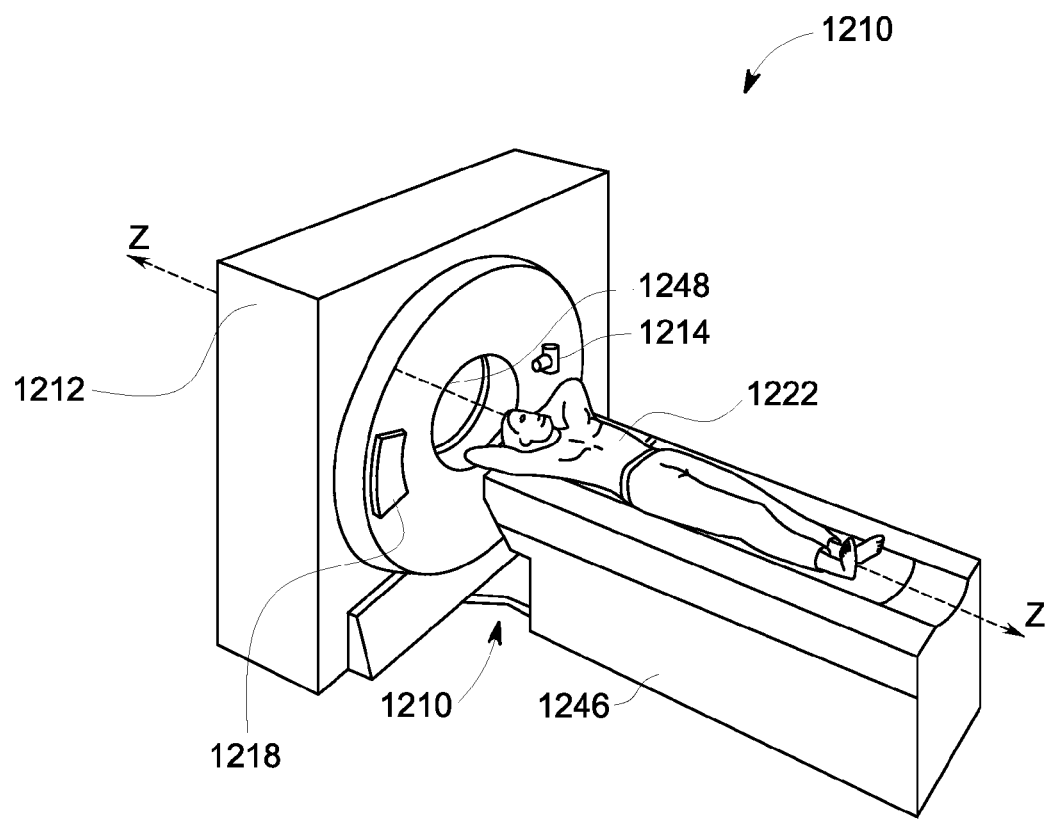
FIG. 13 is a perspective view of a computed tomography (CT) imaging system constructed in accordance with an embodiment.

FIG. 13 is a pictorial view of a CT imaging system 1210 formed in accordance with an embodiment. FIG. 12 is a block schematic diagram of the CT imaging system 1210 illustrated in FIG. 13. In the exemplary embodiment, the CT imaging system 1210 is shown as including the gantry 1212 representative of a "third generation" CT imaging system. The gantry 1212 has the radiation source 1214 that projects a cone beam 1216 of X-rays toward the detector array 1218 on the opposite side of the gantry 1212.

The detector array 1218 is formed by a plurality of detector rows (not shown) including a plurality of detector elements 1220 that together sense the projected X-ray beams that pass through an object, such as a medical patient 1222. Each detector element 1220 produces an electrical signal that represents the intensity of an impinging radiation beam and hence the attenuation of the beam as the beam passes through object or patient 1222. The CT imaging system 1210 having a multislice detector 1218 is capable of providing a plurality of images representative of a volume of patient 1222. Each image of the plurality of images corresponds to a separate "slice" of the volume.

Figure 4:
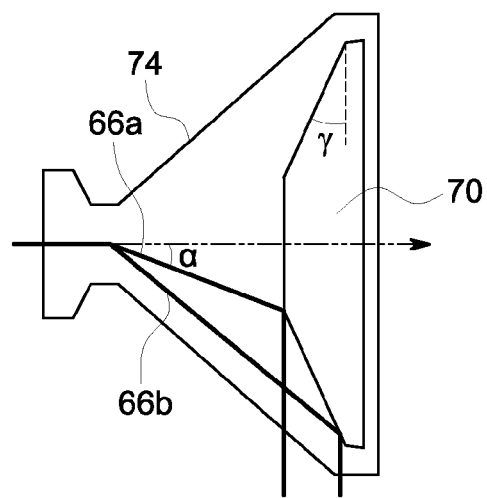
FIG. 4 illustrates a focal spot deflection in an x-ray tube having an increased focal spot spacing in accordance with an embodiment.

During a scan to acquire radiation projection data, the gantry 1212 and the components mounted thereon rotate about a center of rotation 1224 defining a gantry rotation axis (the z-axis or z-direction), illustrated by the dashed line Z in FIG. 13. The z-axis extends into and through the gantry opening 1248. In various embodiments, the radiation source 1214 may include an x-ray tube 60 (shown in FIG. 2-4) that uses focal spot deflection and has a target aligned with the z-axis as described in more detail below. The x-ray tube 60 performs rapid kVp switching producing dual-energy x-rays to reduce mis-registration of high and low energy data with nearly simultaneous acquisition during adjacent view samples. Additionally, the x-ray tube 60 produces high and low x-ray energy with minimal or no overlap.

The various embodiments or components, for example, the components of the CT imaging system of controllers or processors therein may be implemented as part of one or more computer systems, which may be separate from or integrated with other systems. The computer system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device may also be other similar means for loading computer programs or other instructions into the computer system.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also store data or other information as desired or needed. The storage element may be in the form of an information source or a physical memory element within the processing machine.

The set of instructions may include various commands that instruct the computer as a processing machine to perform specific operations such as the methods and processes of the embodiments of the subject matter disclosed herein. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the subject matter disclosed herein without departing from their scope. While the dimensions and types of materials described herein are intended to define the parameters of the various embodiments of the subject matter disclosed herein, the embodiments are by no means limiting and are exemplary embodiments. Many other embodiments will be apparent to those of skill in the art upon reviewing the above description. The scope of the various embodiments of the subject matter disclosed herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the subject matter disclosed herein, including the best mode, and also to enable any person skilled in the art to practice the various embodiments of the subject matter disclosed herein, including making and using any devices or systems and performing any incorporated methods. The patentable scope of the various embodiments of the subject matter disclosed herein is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An x-ray system comprising:
   a field-generator configured to generate a field;
   an electron beam generator configured to generate an electron beam directed towards a target;
   a voltage controller configured to control the electron beam generator to produce an electron beam at a first energy level and an electron beam at a second energy level; and
   a field-generator controller configured to control a field to deflect at least one of the electron beams, wherein the electron beam, at the first energy level, impinges on the target at a first contact position and the electron beam, at the second energy level, impinges on the target at a second contact position, and wherein the target, at the first contact position and at the second contact position, is configured to filter x-rays.

2. The x-ray system of claim 1, wherein the target is configured to provide a first filtration of low energy x-rays at a first lower energy level spectrum and a second filtration of low energy x-rays at a second higher energy level spectrum, wherein the first filtration is less than the second filtration.

3. The x-ray system of claim 1, wherein the electronic circuit is configured to transition from the first voltage to the second voltage within a time of less than 1 second.

4. The x-ray system of claim 1, wherein the first contact position and the second contact position comprise different target materials.

5. The x-ray system of claim 1, wherein the first contact position and the second contact position comprise different target angles.

6. The x-ray system of claim 1, wherein the first contact position and the second contact position comprise target materials of different thickness.

7. The x-ray system of claim 1, wherein the first contact position and the second contact position have at least one of different target materials or different target angles or different thicknesses.

8. The x-ray system of claim 1, wherein the first voltage is between about 60 kVp and about 80 kVp.

9. The x-ray system of claim 1, wherein the second voltage is between about 110 kVp and about 160 kVp.

10. The x-ray system of claim 1 configured as a computed tomographic system.

11. The x-ray system of claim 1, wherein the target is a rotating target.

12. The x-ray system of claim 1, wherein the low energy data and the high energy data are acquired simultaneously.

13. The x-ray system of claim 1, wherein the electron beam deflects between the first contact position and the second contact position in less than 1 second.

14. A method of filtering dual energy x-ray, the method comprising:
    generating electron beams;
    directing the generated electrons beam towards a target;
    controlling the voltage of the electron beams to produce an electron beam at a first energy level and an electron beam at a second energy level;
    generating a field;
    controlling the generated field to deflect at least one of the electron beams, wherein the electron beam, at the first energy level, impinges on the target at a first contact position and the electron beam, at the second energy level, impinges on the target at a second contact position; and
    filtering the x-ray produced at the first contact position using the target and filtering the x-ray produced at the second contact position using the target.

15. The method of filtering dual energy x-ray of claim 14, wherein filtering of the lower energy level spectrum is less than the filtering of higher energy level spectrum.

16. The method of filtering dual energy x-rays of claim 14, wherein transitioning between first voltage and second voltage is done in less than 1 second.

17. The method of filtering dual energy x-ray of claim 14, further comprising providing different target material for the first contact position and the second contact position.

18. The method of filtering dual energy x-ray of claim 14, further comprising providing different target angle for the first contact position and second contact position.

19. The method of filtering dual energy x-ray of claim 14, further comprising providing different target material thickness for the first contact position and second contact position.

20. A target for an x-ray tube, the target comprising:
    a first contact area configured to receive an electron beam having a first energy spectrum, the first contact area configured to provide a first filtration of low energy X-rays at the first energy spectrum; and
    a second contact area different than the first contact area, the second contact area configured to receive an electron beam having a second energy spectrum higher than the first energy spectrum, the second contact area configured to provide a second filtration configured to remove wavelengths associated with the first energy spectrum, wherein the first and second contact areas are formed from different materials or provided at different angles, and configured to receive thereon differently deflected electron beams.

* * * * *